US010391347B2

(12) United States Patent
Roveri et al.

(10) Patent No.: US 10,391,347 B2
(45) Date of Patent: Aug. 27, 2019

(54) PROCESS FOR BIOCHEMICAL DENATURATION OF AN ASBESTOS-CONTAINING MATERIAL

(71) Applicant: LEBSC S.R.L., Bologna (IT)

(72) Inventors: Norberto Roveri, Bologna (IT); Isidoro Giorgio Lesci, Castel Bolognese (IT); Sandra Petraroia, Cercemaggiore (IT); Francesco De Laurentis, Naples (IT); Marco Lelli, Monghidoro (IT); Odila Mezini, Imola (IT); Giulia Montebugnoli, Monterenzio (IT); Selene Merli, Montecarotto (IT); Eros D'Amen, Bologna (IT); Roberto Gallerani, Renazzo di Cento (IT)

(73) Assignee: LEBSC S.R.L, Bologna (IT)

( * ) Notice: Subject to any disclaimer, the term of this patent is extended or adjusted under 35 U.S.C. 154(b) by 162 days.

(21) Appl. No.: 15/306,701

(22) PCT Filed: Mar. 19, 2015

(86) PCT No.: PCT/IB2015/052021
§ 371 (c)(1),
(2) Date: Oct. 25, 2016

(87) PCT Pub. No.: WO2015/166359
PCT Pub. Date: Nov. 5, 2015

(65) Prior Publication Data
US 2017/0043198 A1 Feb. 16, 2017

(30) Foreign Application Priority Data

Apr. 29, 2014 (IT) .............................. MI2014A0789

(51) Int. Cl.
*A62D 3/02* (2007.01)
*A62D 3/36* (2007.01)
*C12P 7/54* (2006.01)
*C12P 7/46* (2006.01)
*A62D 101/41* (2007.01)

(52) U.S. Cl.
CPC ................. *A62D 3/36* (2013.01); *A62D 3/02* (2013.01); *C12P 7/46* (2013.01); *C12P 7/54* (2013.01); *A62D 2101/41* (2013.01); *A62D 2203/02* (2013.01)

(58) Field of Classification Search
CPC .. A62D 3/36; A62D 2101/41; A62D 2203/02; A62D 3/02; C12P 7/54; C12P 7/46
See application file for complete search history.

(56) References Cited

U.S. PATENT DOCUMENTS 6,718,616 B2    4/2004  Craig et al.

FOREIGN PATENT DOCUMENTS

EP    2 428 254 A1    3/2012

OTHER PUBLICATIONS

Favero-Longo et al., "Interactions of sterile-cultured lichen-forming ascomycetes with asbestos fibres", Mycological Research 111: 473-481 (2007).
Heasman et al., "The Destruction of Chrysotile Asbestos Using Waste Acids", Waste Management & Research 4: 215-223 (1986).
Rivas et al., "Tartaric Acid Recovery from Distilled Lees and Use of the Residual Solid as an Economic Nutrient for Lactobascillus", J. Agric. Food Chem. 54: 7904-7911 (2006).
Stanik et al., "Destruction of the Chrysotile Asbestos Structure with a Population of Bacteria Lactobacillus casei and Lactobacillus plantarum", Fresenius Environmental Bulletin 15: 640-643 (2006).
Wu et al., "Biodiversity of yeasts, lactic acid bacteria and acetic acid bacteria in the fermentation of 'Shanxi aged vinegar', a traditional Chinese vinegar", Food Microbiology 30: 289-297 (2012).
Ukuku et al., "Behavior of Native Microbial Populations of WPC-34 and WPC-80 Whey Protein Stored At Different Temperatures", J. Food Process Technol. vol. 3, Issue 3 (2014), pp. 1-5.
Intellectual Property Office of Singapore Search Report for Application No. 11201608535W, dated Jul. 12, 2017.
Intellectural Property Office of Singapore Written Opinion for Application No. 11201608535W, dated Dec. 12, 2017.

*Primary Examiner* — Satyendra K Singh
(74) *Attorney, Agent, or Firm* — Jeffrey N. Townes; Cozen O'Connor

(57) ABSTRACT

The invention relates to a process for treating an asbestos-containing material, which enables the asbestos to be transformed into inert products (i.e. not hazardous to human health) that can possibly be reused as raw materials for subsequent industrial processing or as directly marketable industrial products. The process comprising the steps of preparing an acidic solution/suspension by subjecting a food industry waste material to mixed bacterial and fungal growth and/or fermentation, and treating an asbestos-containing material with the acidic solution/suspension obtained from the mixed fermentation at a temperature of 120-170° C. and pressure of 2-10 bar.

16 Claims, 9 Drawing Sheets

A

B

A

B

A

B

PROCESS FOR BIOCHEMICAL DENATURATION OF AN ASBESTOS-CONTAINING MATERIAL

CROSS-REFERENCE TO RELATED APPLICATIONS

This application is a national-stage application under 35 U.S.C. § 371 of PCT Application No. PCT/IB2015/052021, filed Mar. 19, 2015, which claims priority to Italian Patent Application No. MI2014A000789, filed Apr. 29, 2014, which are hereby incorporated by reference in their entirety.

FIELD OF THE INVENTION

The present invention relates to a process for treating an asbestos-containing material, which enables the asbestos to be transformed into inert products (i.e. not hazardous to human health) that can possibly be reused as raw materials for subsequent industrial processing or as directly marketable industrial products.

BACKGROUND ART

Asbestos is the commercial name attributed to several natural minerals having a fibrous structure and belonging to the class of silicates. In modern times some of these minerals were widely used because of their excellent technological properties: they have good resistance to heat and fire, to the action of chemical and biological agents and to abrasion and wear, display high mechanical strength and good flexibility, easily bind with construction materials and have good sound absorbing and heat insulating properties. Because of all these properties and its low cost asbestos was widely used in manufactured products and industrial and building applications, in means of transport and in the domestic sphere. In particular, the raw fibre was processed in order to obtain various products adaptable to multiple uses. In these products, the asbestos fibres may either be free, or strongly or weakly bound. If they are weakly bound, they are referred to as friable materials, which can be crumbled by hand pressure alone due to the poor internal cohesion. If they are strongly bound, they are referred to as compact materials, which can be crumbled into powder only with the aid of machinery. The materials in a friable matrix are undoubtedly the most dangerous, as the fibres can be dispersed into the air with extreme ease and thus inhaled. Asbestos in a compact matrix, given its nature, does not tend to release fibres and a hazardous situation may arise only if it is abraded, deteriorated or sawed. There are a vast number of types of Asbestos-Containing Materials (ACM) which have extremely varied and differentiated characteristics and uses. The U.S. Federal Register lists over 3000 finished objects which contain asbestos. ACM can be classified into three categories:

(a) Surface Materials: these include ACM sprayed or distributed by spreading over surfaces (weight-bearing elements, walls, ceilings) for soundproofing, heat insulating and decorative purposes;
(b) Heat Insulation Materials: these include the ACM used to prevent the formation of condensate in pipes, ducts, boilers, tanks and in various components of water cooling systems, as well as in heating, ventilation and air conditioning systems;
(c) Sundry Materials: this category embraces all of the other ACM, as in false-ceilings, sheaths, fabrics, etc.

Asbestos has been undoubtedly most widely used in the building sector, in particular in the form of a composite of asbestos and cement, or so-called asbestos-cement. Moreover, in order to avoid or limit damage to constructions in the event of a fire, asbestos was largely used as a coating on beams or floors, applied with spraying and spreading techniques. The heat-resistant mixture was composed of varying percentages of asbestos and other materials (vermiculite, sand or cellulose fibres) and binding materials (gypsum and/or calcium carbonate): the result was a continuous layer, soft to the touch, of a colour varying from dark grey to white. Asbestos minerals were used as additives in cement conglomerates to improve their mechanical characteristics: the phases were usually Portland cement, water, aggregates and fibres of Chrysotile, Crocidolite and/or Amosite (more rarely), until eventually only Chrysotile was used. The asbestos content was variable and could reach 50% by weight depending on the type of product to be obtained.

Today it is a universally recognized the fact that asbestos is one of the materials most hazardous to human health among those present in living and work environments; this hazard results in severe pathologies prevalently affecting the respiratory tract. Although an etiological connection between the inhalation of airborne asbestos fibres and the onset of specific diseases was already hypothesized at the start of the last century, it was not until the 1990s that regulations consistent with the hazardousness of the material were introduced in various countries.

Ascertainment of the harm that this raw material caused to workers obliged the governments of all countries in the world to address the problem, in consideration of the exceedingly high social costs ensuing from occupational diseases developed by industry operators over the years.

It should be noted that the accumulation of Asbestos-Containing Waste (ACW) in landfills does not solve the problem, but rather simply passes it on to future generations: it is thus important to devise a strategy that allows ACW to be transformed and subsequently exploited as materials in the production of new products which are totally safe from an environmental viewpoint.

There are currently in use a number of processes, in addition to ACW "inertization" and "isolation", which are suitable for transforming it and have the aim of completely eliminating the hazardousness thereof. "Inertization" processes include procedures for conditioning in matrices of varying nature which prevent the dispersal of asbestos fibres in the environment, whereas "transformation" processes act directly upon the fibrous structure of the mineral itself, transforming it into other phases that are not hazardous to human health.

The main ACW transformation processes are based on chemical treatments relying on the action of acids and thermal and mechanochemical treatments, though recently biochemical and microbiological methods have been devised.

Insofar as regards acid treatments, various methods have been developed which envisage the use of both organic and mineral acids to transform ACW so as to obtain secondary materials that are recyclable and often reusable in the ceramics industry. In particular, the effects of mineral acids, such as hydrofluoric, hydrochloric and sulphuric acid, as well as the effects of organic acids such as formic and oxalic acid, have been studied. As regards thermal treatments, it is well known that asbestos materials are unstable at high temperatures. Chrysotile, for example, has a tendency to lose the hydroxyl groups at around 600° C. and to be transformed into a different inert mineral phase, Forsterite, which is recrystallized at 820° C. The application of this principle makes it possible to obtain inert materials from ACW, as such or ground, treated in furnaces at a temperature of 800-950° C. Furthermore, if heating is preceded by compacting of the material, the consequent disorientation of the crystals allows the final product to be used as electrical insulation or refractory material. This process takes the name of ceramization. It is also possible to achieve a vitrification of ACW through a number of processes which are based on melting asbestos-containing waste with the addition of different additives within a broad temperature interval (1300-1800° C.), followed by rapid cooling with the production of an inert material having an amorphous vitreous structure. However, this solution requires a great deal of energy in order to bring the melting ovens to extremely high, constant temperatures.

In vitroceramization, on the other hand, the waste is melted at temperatures of between 1300 and 1400° C. together with particular additives, such as blast furnace slag or industrial sludge, forming a mixture with a high metal content. The slag thus derived is made to crystallize at a controlled temperature: in this manner one obtains products with very high mechanical strength, particularly suitable as coating and protective surfaces in the building, mechanical and chemical industries.

Another technique consists in so-called lithification, which is based on melting ACW derived from the removal of insulation from railway carriages at a temperature of 1300-1400° C. Slow cooling brings about a crystallization of pyroxenes, olivine and iron oxides. The final result of the treatment is the production of inert materials, which can be recovered for a variety of applications.

As regards biological treatments, the microbiological action of mosses and lichens on different rocky substrates containing asbestos fibres has been studied both in vivo and in vitro: the hyphae of lichens and fungi are capable of penetrating and secreting chemical compounds (oxalic acid is one of the primary metabolites), some of which can alter the mineralogical structure of asbestos fibres (see for example the article by S. E. Favero-Longo, M. Girlanda, R. Honegger, B. Fubini, R. Piervittori; Mycological Research, Vol. 111, Issue 4, pp. 473-481 (2007)).

Microbiological methods have also been developed for the transformation of asbestos using bacteria, in particular *Lactobacillus casei* and *Lactobacillus plantarum* (see for example the article by I. A. Stanik, K. Cedzyńska, S. Żakowska; Fresenius Environmental Bulletin, Vol. 15, Issue 7, pp. 640-643 (2006)). The method is based on breaking down the crystalline layers of Brucite (magnesium-oxygen) present within the crystalline layers of Chrysotile as a consequence of the indirect metabolism of the bacterial cultures used. The decomposition of crystalline layers seems to be due to the acidification of the reaction environment, thanks to the presence of metabolites secreted by the bacteria, which also include lactic acid. The hypothesized reaction mechanism is achieved through a substitution of $Mg^{2+}$ ions by $H^+$ ions, which are present in great excess. The magnesium thus released reacts with the lactic acid present to form soluble salts.

One of the microbiological processes for decomposing asbestos fibres (mainly Chrysotile) contained within asbestos-cement products was patented by Chemical Center S.r.l. (European patent: EP2428254), a company operating in the sector of analysis and in particular eco-innovation.

The process envisages using amounts of exhausted milk whey having an acidic pH to break down the cementitious phase (85%) and release the asbestos fibres (15%) incorporated therein, fibres which are then denatured and broken down into magnesium ions and silicate using further amounts of exhausted milk whey in a hydrothermal process. The overall process can be divided into two steps: 1) decomposing the calcium carbonate so as to release the asbestos fibres in water and 2) decomposing the asbestos fibres.

Unfortunately, the methods for transforming asbestos-containing materials (ACM) known to date present non-negligible disadvantages. In particular, acid treatments lead to the accumulation of a large amount of waste products, which also need to be disposed of. Furthermore, it should be kept in mind that in order to treat millions of tons of ACW (the approximate estimate for Italian territory alone ranges between 20 and 30 million tons) it would be necessary to use enormous amounts of reagents, which would entail non-negligible environmental risks and very high costs. With regard to thermal treatments, the largest disadvantage, besides the enormous amount of energy required to bring the furnaces to very high, constant temperatures, is given by the fact that suitable equipment is often polluting and highly costly and thus scarcely available across the territory, so that it is necessary to transport the ACW over long distances, with the consequent environmental risks and logistical costs.

The processes that use biochemical and microbiological methods (including the process that envisages using milk whey) also present several disadvantages, such as, for example, a low degree of transformation of the asbestos fibres, sometimes occurring only superficially without reaching a complete transformation. Therefore, such methods have not found to date any applications that are feasible on an industrial scale.

In particular, the use of bacterial microflora of *Lactobacillus* (envisaged in the method of EP2428254 and in the article of I. A. Stanik et al. Fresenius Environmental Bulletin, Vol. 15, Issue 7, pp. 640-643 (2006)), requires a culture temperature of 37° C. in order to obtain acidic metabolites, particularly lactic acid, and reach an acidic pH that is efficient in decarbonising the calcite phase of the asbestos-containing material. Moreover, the culture times for obtaining a microbial population that is sufficient for denaturing are generally long.

In addition, a characteristic of milk whey that is disadvantageous for denaturing an asbestos-containing material is the lipid component, which, by forming micelles of fat at the water-air interface, causes a slowdown in the carbon dioxide decarboxylation reaction and thus an equilibrium toward the re-precipitation of calcite.

Moreover, the excessive biological component, both lipidic and proteic, interacts with the asbestos fibres, enveloping them with a protective biofilm, packing them together and making the denaturing thereof through an ionic exchange reaction more difficult.

Ultimately, milk whey is mostly used for zootechnical nutrition and only in certain periods of the year is there a certain availability in the market as actual waste from dairy production.

SUMMARY OF THE INVENTION

The invention aims to overcome the limits and disadvantages of the known prior art solutions for the treatment of transforming and inertizing asbestos-containing materials, in particular the above-described methods envisaging the use of bacterial microflora, by providing a process for treating asbestos-containing materials comprising a single step for treating the asbestos-containing material with a acidic solution/suspension obtained via mixed bacterial and fungal growth and/or fermentation of a food industry waste material.

The food industry waste material is preferably selected from: liquid/solid waste from vinegar production, liquid/solid waste from wine production, waste from oil production (for example, mill wastewater), liquid/solid waste from fruit and vegetable processing and preservation (for example, the water for blanching tomato skins and citrus fruit peels), liquid/solid waste from the production of beer, beverages and fruit-based juices, liquid waste from the oil and vegetable and animal fat refining industry, liquid/solid waste from used tea leaves and from the confectionary industry, liquid/solid waste from rice processing and liquid/solid waste from tobacco manufacturing.

The waste material obtained from food industry processing is subjected to mixed bacterial and fungal fermentation, preferably by means of bacteria of the species *Acetobacter aceti* and yeast of the species *Saccharomyces cerevisiae*, which enables the formation of acids, acetic acid in particular, in a short time.

Once an acidic solution/suspension is obtained by mixed fermentation, the asbestos-containing material is treated with the acidic solution/suspension under conditions of high temperature and pressure.

A solid aluminium silicate- and phosphate-based precipitate and a solution containing metal ions, namely, iron, magnesium, nickel, manganese and calcium is formed during this process.

The solid phase can be reused in industry for the production, for example, of cement, after bubbling carbon dioxide through it to enrich it with carbonates, whereas the metal ions contained in the solution can be extracted electrochemically and reused as metals in various applications or precipitated in the form of hydroxides and carbonates and then used for various industrial applications, for example for the preparation of water-based paints.

The asbestos-containing material preferably subjected to the treatment process of the invention is asbestos-cement.

BRIEF DESCRIPTION OF THE FIGURES

The invention will be illustrated in detail below, also with reference to the appended figures, in which.

DETAILED DESCRIPTION OF THE INVENTION

Figure 1:
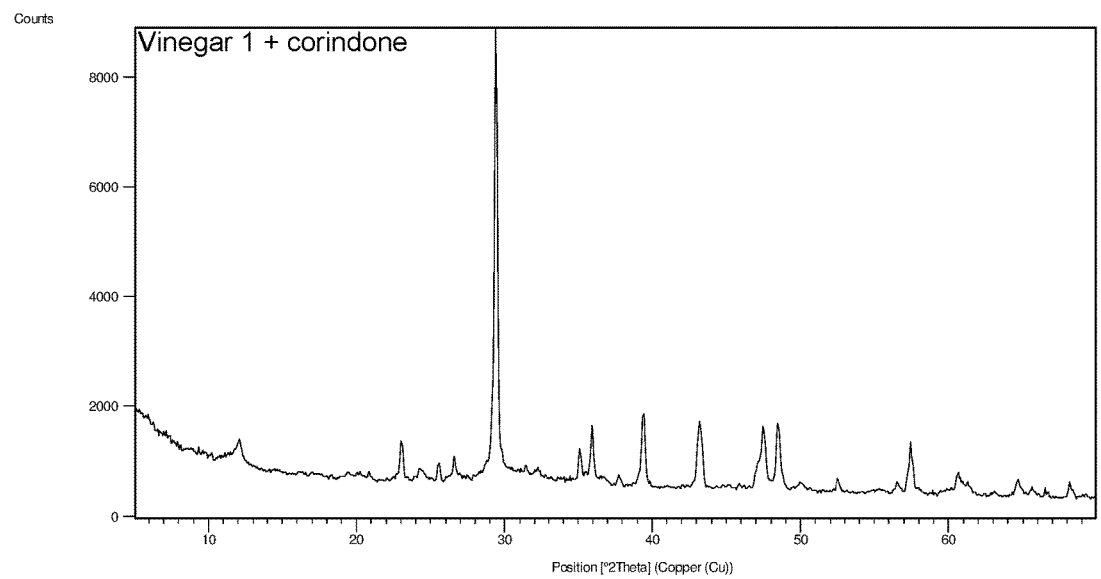
FIG. 1 shows the initial mineral phases (A) and the final crystalline phases (B) of the denaturation process of the invention, carried out by means of acidic solutions deriving from mixed fermentation of vine prunings used for the production wine vinegar (example 1)
Figure 1:
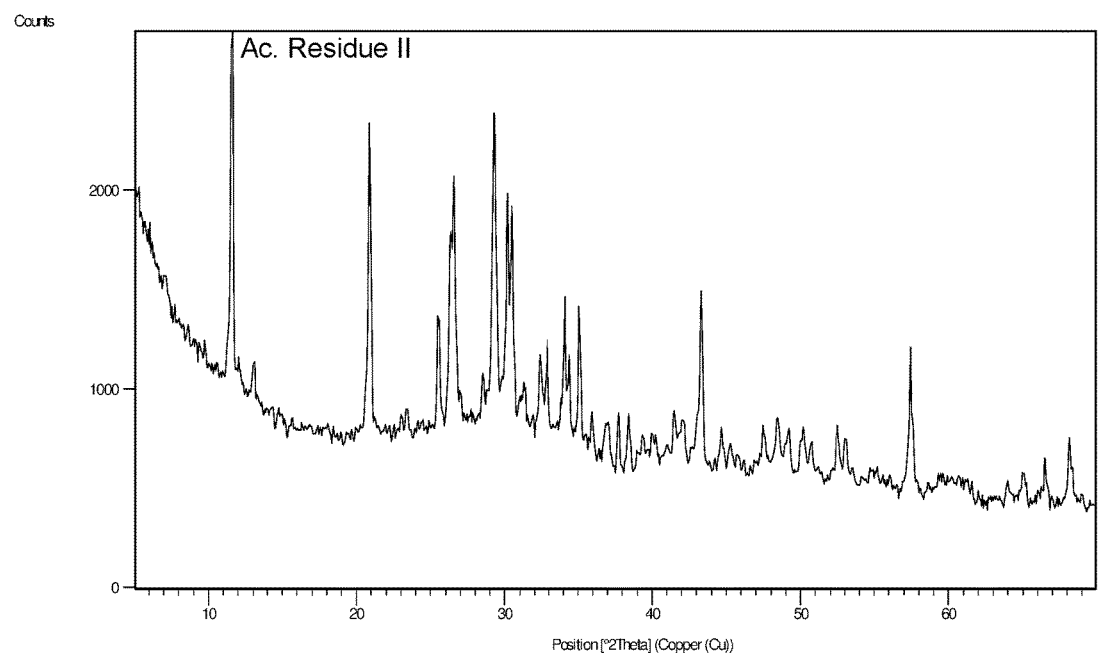

The present invention relates to a process for treating an asbestos-containing material, comprising the steps of:
1) preparing an acidic solution/suspension by subjecting a food industry waste material to mixed bacterial and fungal growth and/or fermentation, preferably by using bacteria of the species *Acetobacter aceti* and yeast of the species *Saccharomyces*;
2) treating an asbestos-containing material with the acidic solution/suspension obtained from the mixed fermentation, preferably at a temperature of 120-170° C. for a period of 1-24 hours and under pressure.

The food industry waste material is preferably selected from: liquid/solid waste from vinegar production, liquid/solid waste from wine production, waste from oil production (for example, mill wastewater), liquid/solid waste from fruit and vegetable processing and preservation (for example, the water for blanching tomato skins and citrus fruit peels), liquid/solid waste from the production of beer, beverages and fruit-based juices, liquid waste from the oil and vegetable and animal fat refining industry, liquid/solid waste from used tea leaves and from the confectionary industry, liquid/solid waste from rice processing and liquid/solid waste from tobacco manufacturing.

The asbestos-containing material which can be subjected to the treatment process of the invention includes asbestos in fibril form dispersed in a friable matrix or a cement matrix, or else in a compact polymer-type matrix. Preferably, the asbestos-containing material is asbestos-cement.

The mixed bacterial and fungal growth and/or fermentation can also be carried out using one or more of the following bacterial species, alone or in combination (also with the species *Acetobacter aceti*): *cerevisiae* Micrococcaceae, Propionibacteria, Bifidobacteria, *Pseudomonas* spp., *Aeromonas* spp., *Photobacterium* spp., *Achromobacter* spp., *Shewanella* spp., *Xanthomonas* spp., *Vibrio* spp., *Flavobacterium* spp., *Enterobacteriaceae*, *Bacillus* spp., *Clostridium* spp., *Brochothrix thermosphacta*, *Micrococcus* spp., lactic bacteria in general and in any case all microorganisms classified as extreme acidophiles and acidophiles present in food industry waste.

The mixed bacterial and fungal growth and/or fermentation is carried out by incubating the food industry waste material preferably at a temperature of between 15 and 25° C., for a time varying from a few minutes to a few hours or a few days depending on the type of food waste used. During this step, which requires a limited amount of time, the formation of acids, acetic acid in particular, takes place. One thus obtains an acidic solution/suspension having a pH of between 0 and 6, preferably about 2, also depending on the quantity and quality of sugary nutrients that can or must be added to the solution to increase the metabolic activity of the microorganisms.

Besides the formation of acids, during fermentation it is possible to observe the development of a microbial population that is preserved over time and is able to survive at higher pHs.

The combination of the acidic pH and the microbial concentration makes it possible to obtain a solution/suspension capable of providing excellent results in terms of degradation of the asbestos-containing material, in a decidedly shorter amount of time than with the known processes.

After fermentation the acidic solution/suspension is placed in contact with the asbestos-containing material, preferably in a closed reactor, in an acid solution/asbestos-containing material ratio of between 2 and 10, preferably at a temperature of 120-170° C. for a period of 1-24 hours, and preferably under a pressure of between 2 and 10 bar.

During this step of the process, a decarboxylation (denaturation) of the asbestos-containing material occurs, in which the calcium ions are almost totally re-precipitated in mineral phases according to the initial percentage of calcite. This prevents a reverse reaction and hence the re-formation of calcite which would result, in part, in the packing of the fibres. Moreover, the calcium ions are not adsorbed as micronutrients by the bacterial flora. The magnesium prevalently remains in the solution in an ionic form available for recovery via an electrochemical process. Compared to the known transformation process carried out with milk whey, the concentration of magnesium obtained with the method of the invention is greater.

The solution/suspension deriving from the fermentation, not being rich in lipids, enables carbon dioxide to be released in a shorter amount of time and at lower temperatures than the known process that uses milk whey, since there is a reduced formation of the biofilm of lipidic and proteic origin. This is an advantage in terms of the industrial applicability of the process and degradation efficiency.

The acidic solution deriving from the microbial and mycotic activity can be easily regenerated by reactivating the fermentation of the food industry waste material, thus enabling a greater availability thereof and a reduced processing cost.

Preferably, the asbestos-containing material is pulverized before being treated with the acidic solution/suspension deriving from the fermentation. The higher the degree of crushing of the asbestos-containing material is, the faster its transformation will be. Crushing of the asbestos-containing material can take place under water misting and vacuum conditions to avoid any emission of fibres into the air, preferably in a number of steps in which the asbestos-containing material is first crushed with a large particle size and then pulverized into dimensions of less than one millimeter.

Then follows a homogenization of the asbestos-containing material with the acidic solution/suspension. After homogenization a decarbonisation of the asbestos-containing material takes place, with the effect of producing $CO_2$ and creating a suspension of fibrous asbestos material in solution. The suspension, preferably in the same reaction chamber, is heated under a pressure of 2-10 bar at 120-170° C. for 1-24 hours until there is a total chemical conversion of the asbestos fibres into calcium phosphates and aluminium silicates.

The temperature of 120-170° C. is preferably reached by applying a temperature gradient of 20° C. to 170° C., preferably with a single treatment cycle.

At the end of the treatment a solution and a solid precipitate are obtained. The solution contains iron, magnesium, nickel, manganese and calcium ions, whereas the solid precipitate contains aluminium silicates and phosphates.

The solid precipitate can be subjected to carbon dioxide bubbling so as to enrich it with carbonates and make it usable, for example, as a clinker for cement.

The metal ions present in the solution deriving from the denaturation of the asbestos-containing material can be precipitated as metal hydroxides, for example, to prepare water-based paints or fertilizers, or extracted electrochemically as pure metallic elements and then reused as metals for various industrial applications.

EXAMPLE 1

Liquid/Solid Waste from Vinegar Production

The residual microorganisms deriving from the waste from vinegar production are made to grow and ferment by incubating the waste material in water and in the presence of woody material coming from the pruning of vines used for wine vinegar production. The temperature for the growth and fermentation of the microorganisms is between 15 and 25° C., for a period in the range of between 24-48 ore. The formation of acids, in particular acetic acid and tartaric acid, takes place during this step. One thus obtains an acidic solution/suspension having a pH of between 0 and 6, preferably 2, also depending on the quantity and quality of sugary nutrients that can or must be added to the solution to increase the metabolic activity of the extreme acidophiles and acidophiles. 10 grams of asbestos-cement powder with 100 ml of the acidic solution deriving from the fermentation of vine prunings used for wine vinegar production was mixed for 14-20 hours at 125° C.-170° C. and 5-9 bar. At the end of the reaction a complete transformation of the asbestos and the formation of new minerals was observed, as shown in FIGS. 1 and 2.

Figure 2:
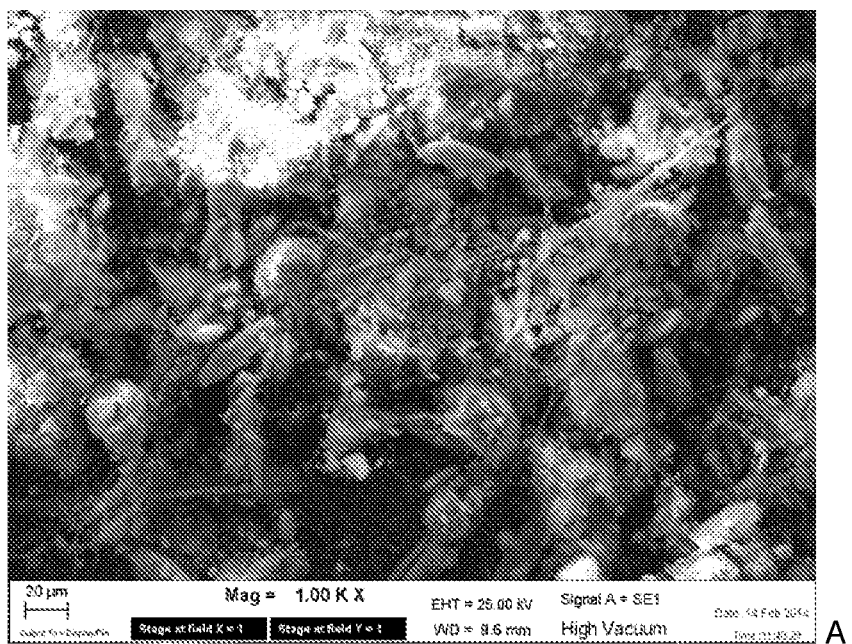
FIG. 2 shows SEM images of the morphology of the asbestos-cement before the transformation (A) and after the treatment of example 1 (B)
Figure 2:
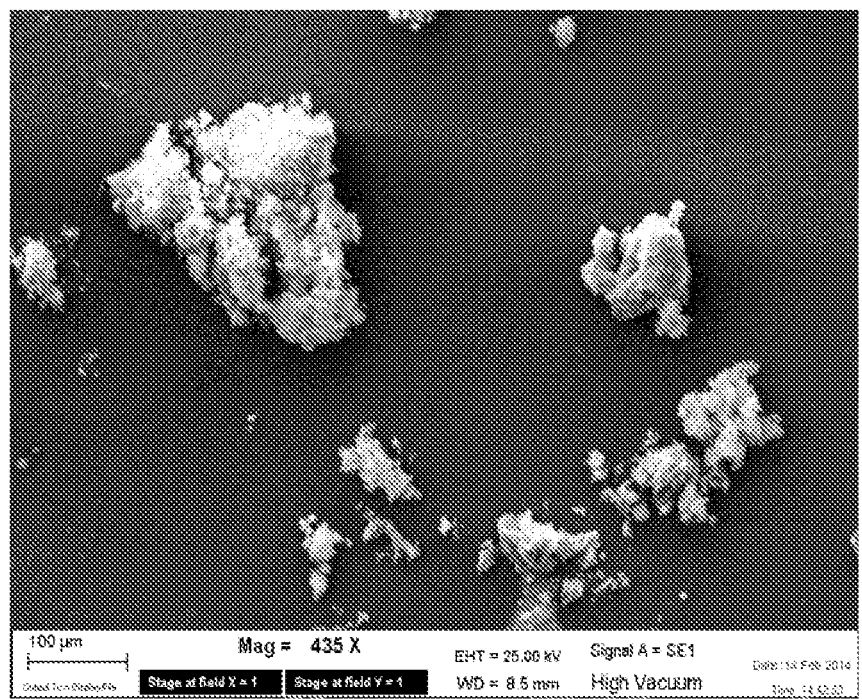

FIG. 1 shows the initial mineral phases (A) and the final crystalline phases (B) obtained by means of acidic solutions deriving from the fermentation of vine prunings used for wine vinegar production; FIG. 2 shows the SEM images of the morphology of the asbestos-cement before the transformation (A) and after the treatment (B).

The crystalline phases before and after the hydrothermal treatment are listed in table 1.

TABLE 1

| Crystalline phases before denaturation | Crystalline phases after hydrothermal transformation |
|---|---|
| Calcite | Brushite |
| Chrysotile | Monetite |
| Quartz | Calcite |
|  | Quartz |

Figure 3:
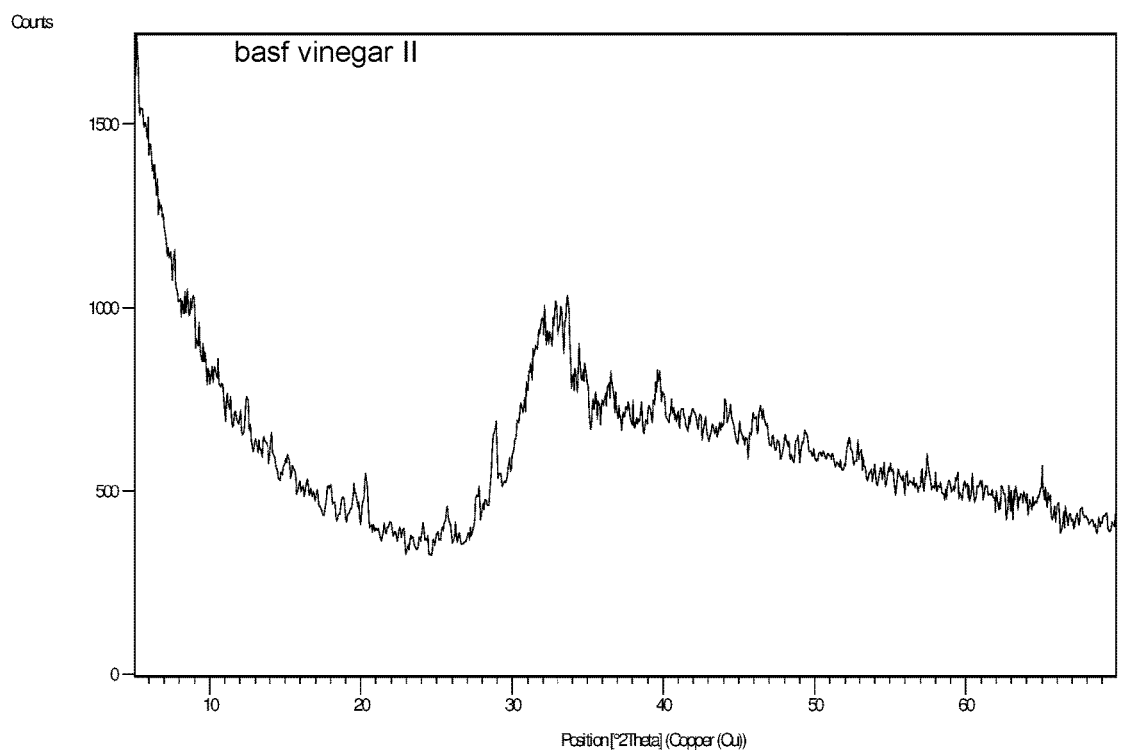
FIG. 3 shows carbonate hydroxyapatite deriving from the supernatant solution obtained as described in example 1 by precipitation in a basic environment.

The solution resulting from the above-described process was treated with sodium hydroxide in order to obtain a water-based paint as illustrated in FIG. 3, which shows carbonate hydroxyapatite deriving from the supernatant solution by precipitation in a basic environment.

Metals can be recovered electrochemically by treating the supernatant solution, as indicated in table 2.

TABLE 2 concentration in mg/l of the electrochemically recoverable metal ions.

| Metallic element | Concentration mg/l |
|---|---|
| Magnesium | 1024.82 |
| Iron | 5.01 |
| Nickel | 4.43 |
| Manganese | 26.65 |

EXAMPLE 2

Waste from Wine Production

The mixed bacterial and fungal fermentation is carried out by incubating the liquid/solid waste material (pomace) in water preferably at a temperature of between 15 and 25° C., for a period of between 24 and 48 hours. The formation of acids, in particular acetic acid and tartaric acid, takes place during this step. One thus obtains an acidic solution/suspension having a pH of between 0 and 6, preferably 2, also depending on the quantity and quality of sugary nutrients that can or must be added to the solution to increase the metabolic activity of the extreme acidophiles and acidophiles.

10 grams of asbestos-cement powder with 100 ml of solution deriving from the fermentation of pomace, liquid/solid waste of wine and/or grappa production, are mixed and made to react for 14-20 hours at 125° C.-170° C. and 5-9 bar. At the end of the reaction the complete transformation of asbestos and formation of new minerals were observed, as shown in FIGS. 4 and 5.

Figure 4:
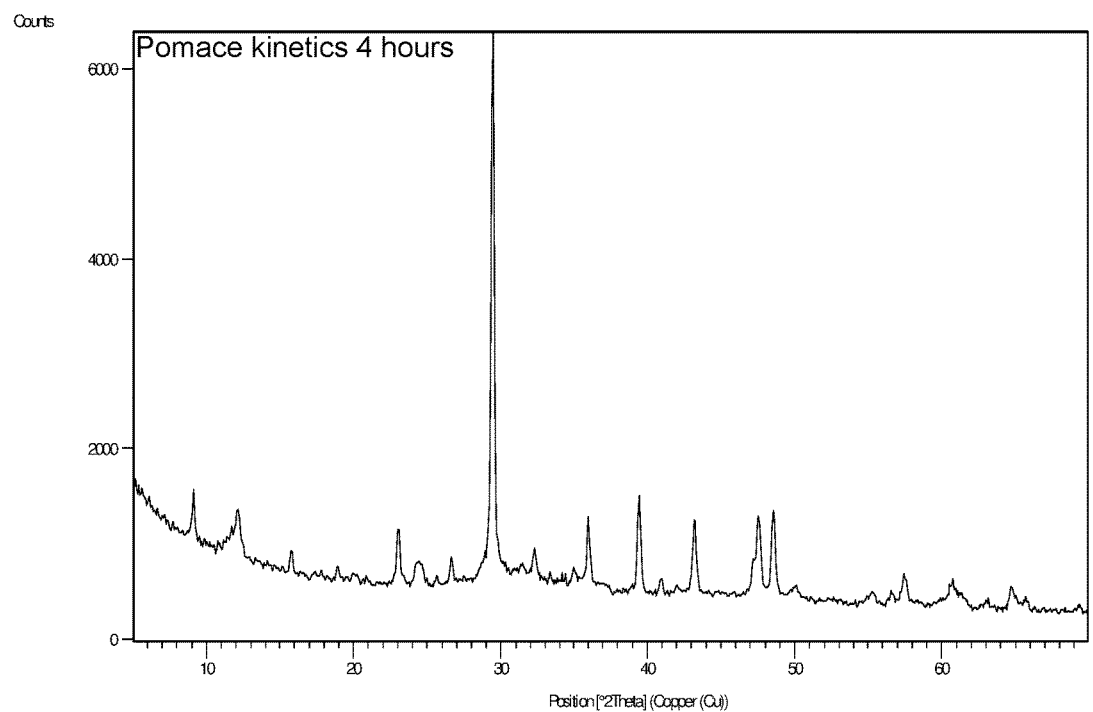
FIG. 4 shows the initial mineral phases (A) and final crystalline phases (B) of the denaturation process carried out by acidic solutions deriving from pomace after the wine extraction and/or grappa maturation.
Figure 4:
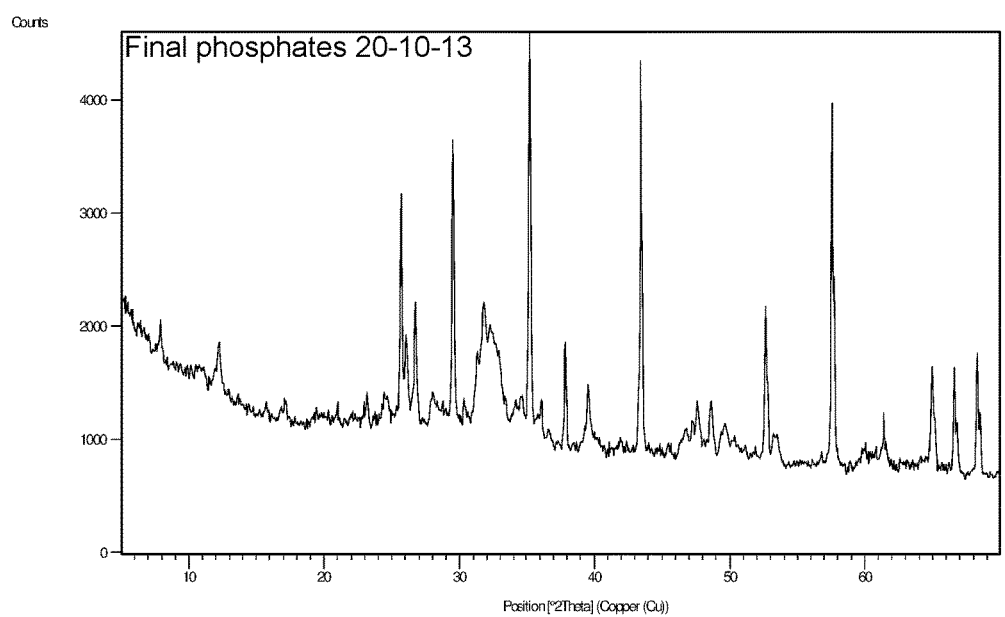
Figure 5:
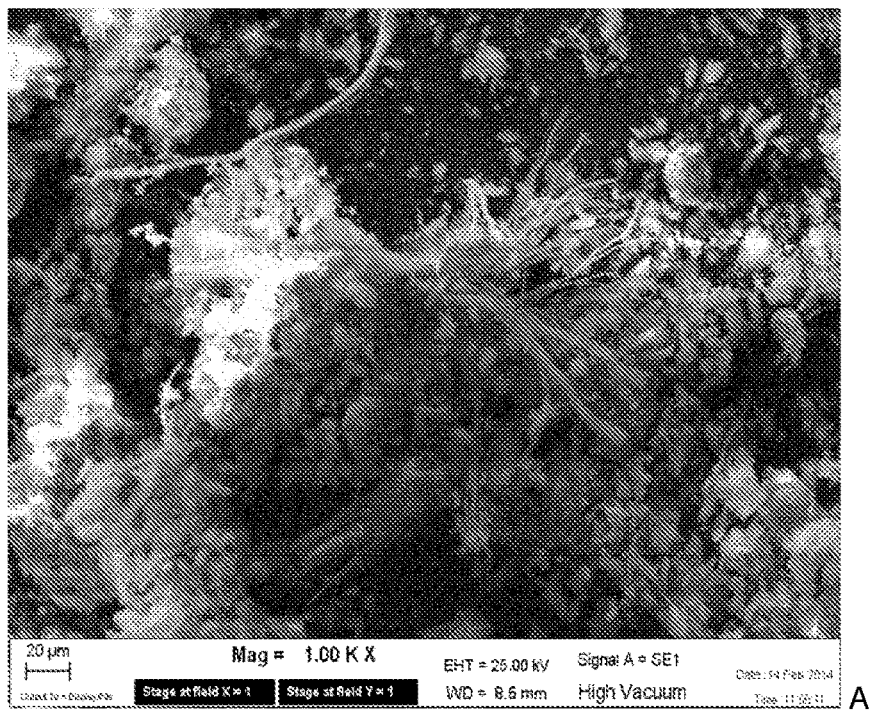
FIG. 5 shows SEM images of the morphology of the asbestos-cement before the transformation (A) and after the hydrothermal treatment (B) according to example 2.
Figure 5:
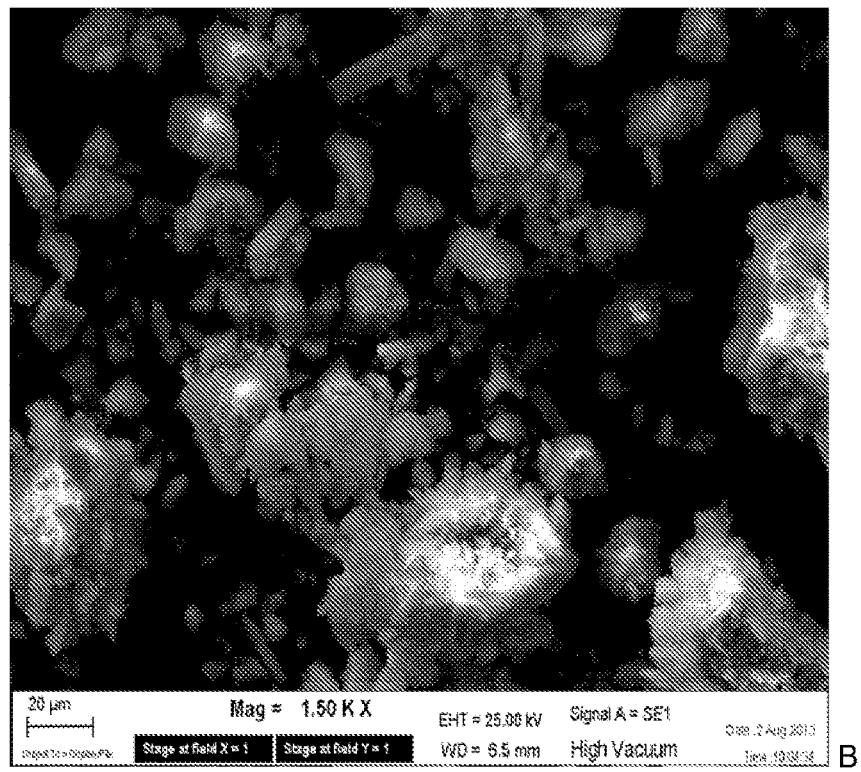

FIG. 4 shows the initial mineral phases (A) and the final crystalline phases (B) of the denaturation process carried out by acidic solutions obtained from the fermentation of pomace after wine extraction and/or grappa maturation, whereas FIG. 5 shows the SEM images of the morphology of the asbestos-cement before the transformation (A) and after the hydrothermal treatment (B).

The crystalline phases before and after the hydrothermal treatment are listed in table 3.

TABLE 3 crystalline phases of the asbestos-cement before and after the denaturation process.

| Crystalline phases before denaturation | Crystalline phases after hydrothermal transformation |
| --- | --- |
| Calcite | Calcium hydrogen phosphate |
| Chrysotile | Hydroxyapatite |
| Ettringite | Quartz |
| Quartz | |

Figure 6:
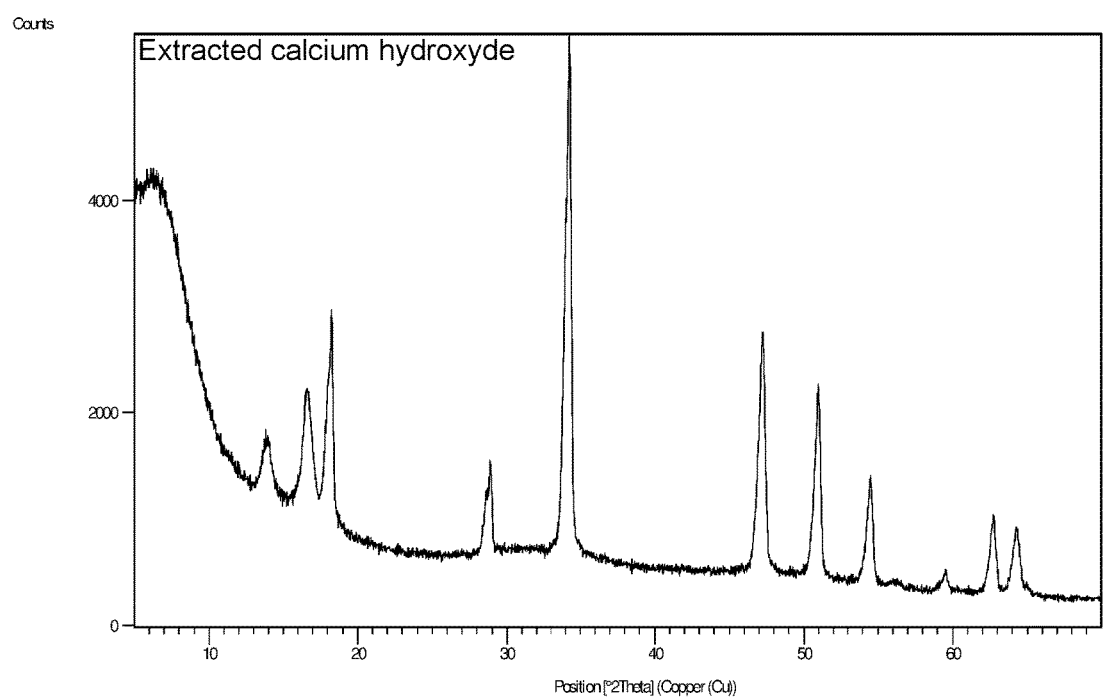
FIG. 6 shows the diffractogram of a water-based paint of calcium hydroxide precipitated from the supernatant solution of example 2.

The liquid resulting from the above-described process is treated with sodium hydroxide to obtain a water-based paint of calcium hydroxide as illustrated in FIG. 6, which shows the diffractogram of the water-based paint of calcium hydroxide precipitated from the supernatant solution.

Metals can be recovered electrochemically from the treatment of the final liquid, as indicated in table 4.

TABLE 4 concentration mg/l of the metal ions recoverable electrochemically.

| Metal element | Concentration mg/l |
| --- | --- |
| Magnesium | 1941.71 |
| Iron | 17.26 |
| Nickel | 2.30 |
| Manganese | 9.10 |

EXAMPLE 3

Processing Waste from Canneries

The residual microorganisms deriving from the processing waste of canneries are made to grow and ferment by incubating the liquid/solid waste material in water. The temperature for the growth and fermentation of the microorganisms is between 15 and 25° C., for a period in the range of 8-24 hours. During this step, the formation of acids, in particular acetic acid, takes place. One thus obtains an acidic solution/suspension having a pH of between 0 and 6, preferably about 2, also depending on the quantity and quality of sugary nutrients that can or must be added to the solution to increase the microbial activity of the extreme acidophiles and acidophiles.

10 grams of asbestos-cement powder with 100 ml of acidic solution obtained from the fermentation of water for blanching tomato skins are mixed and made to react for 14-20 hours at 125° C.-170° C. and 5-9 bar. At the end of the reaction the complete transformation of asbestos and formation of new minerals were observed, as shown in FIGS. 7 and 8.

Figure 7:
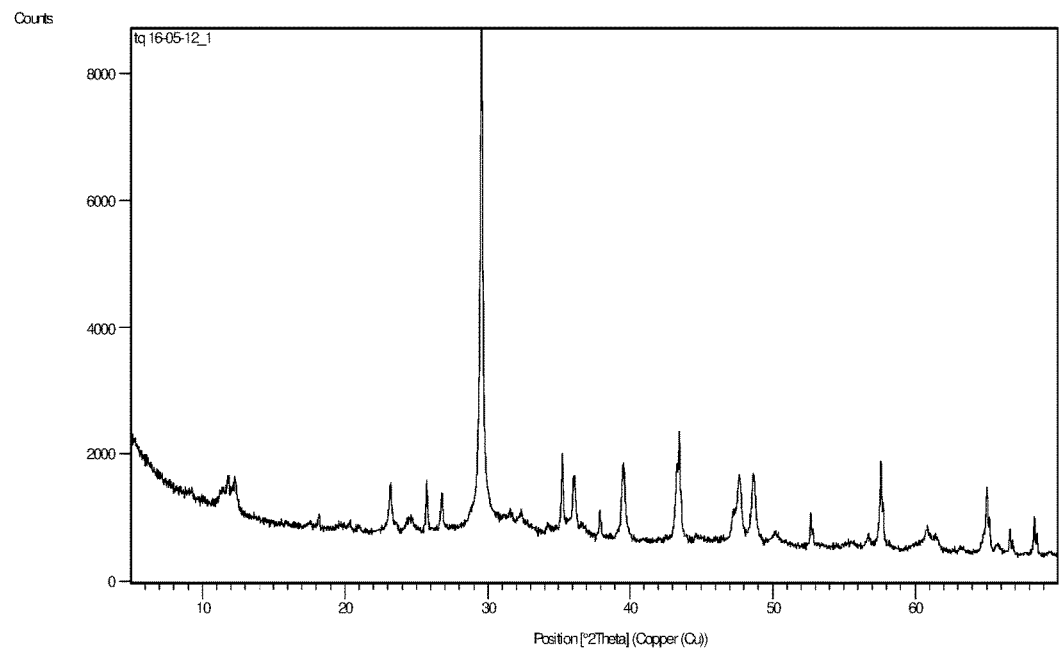
FIG. 7 shows the initial mineral phases (A) and the final crystalline phases (B) of the denaturation process carried out by acidic solutions deriving from the fermentation of water for blanching tomato skins (example 3)
Figure 7:
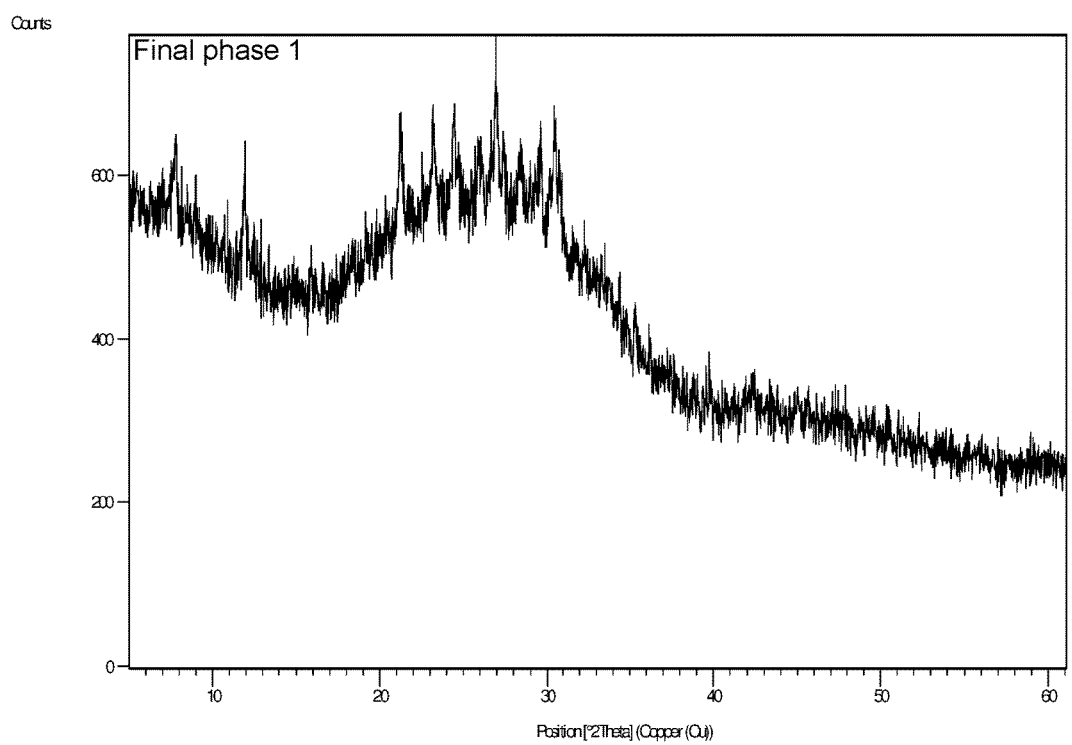
Figure 8:
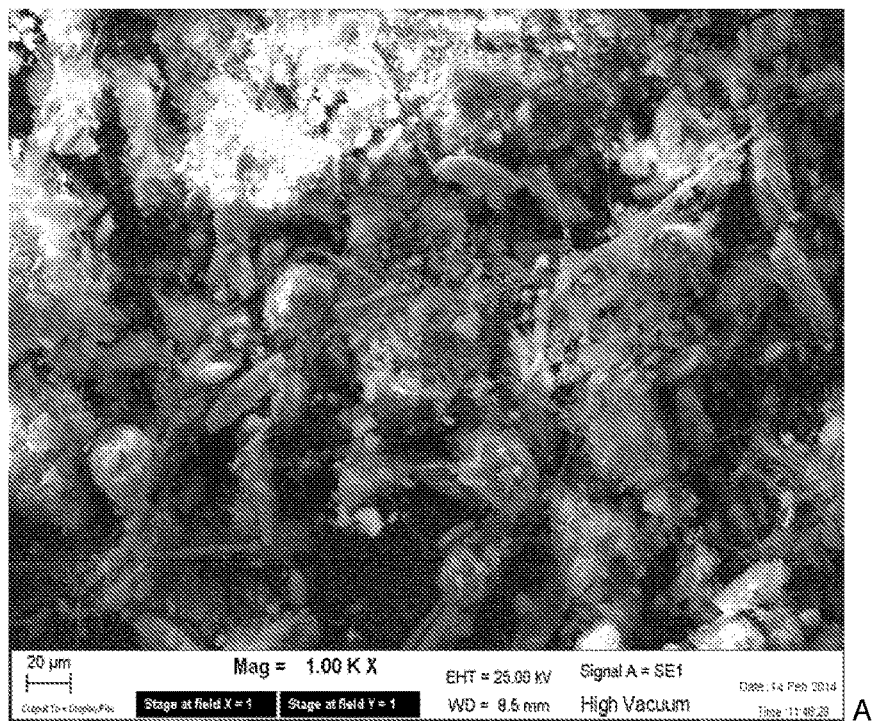
FIG. 8 shows SEM images of the morphology of the asbestos-cement before the transformation (A) and after the hydrothermal treatment (B)
Figure 8:
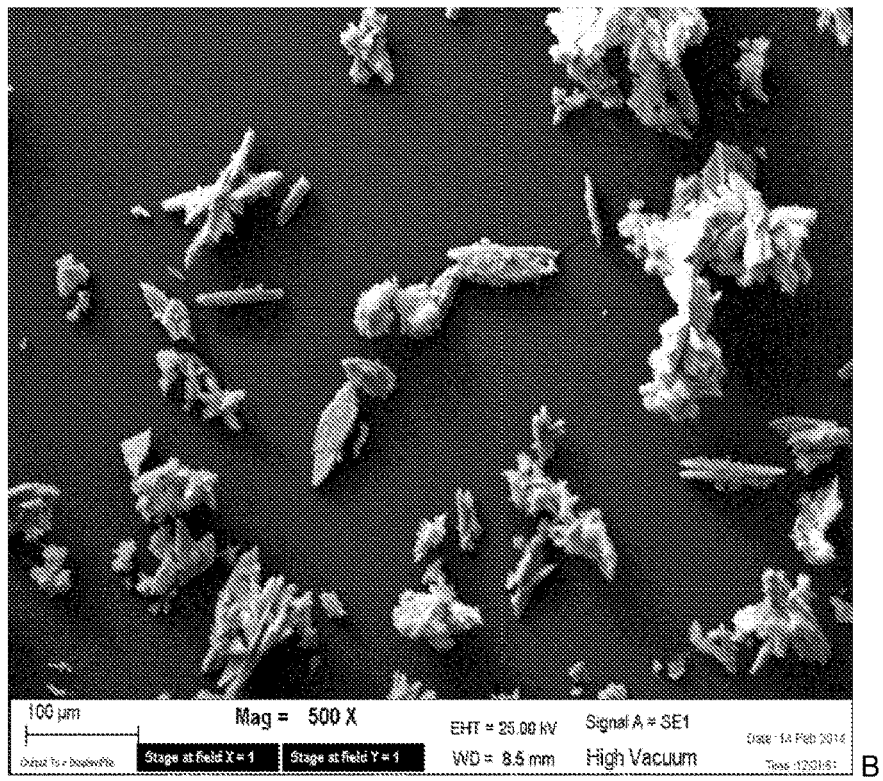

FIG. 7 shows the initial mineral phases (A) and the final crystalline phases (B) of the denaturation process carried out by acidic solutions deriving from fermentation of the water for blanching tomato skins; FIG. 8 shows the shows the SEM images of the morphology of the asbestos-cement before the transformation (A) and after the hydrothermal treatment (B).

The crystalline phases before and after the hydrothermal treatment are listed in table 6.

| Crystalline phases before denaturation | Crystalline phases after the hydrothermal transformation |
| --- | --- |
| Calcite | Calcium hydrogen phosphate |
| Chrysotile | Calcium hydroxyapatite |
| Quartz | |

Figure 9:
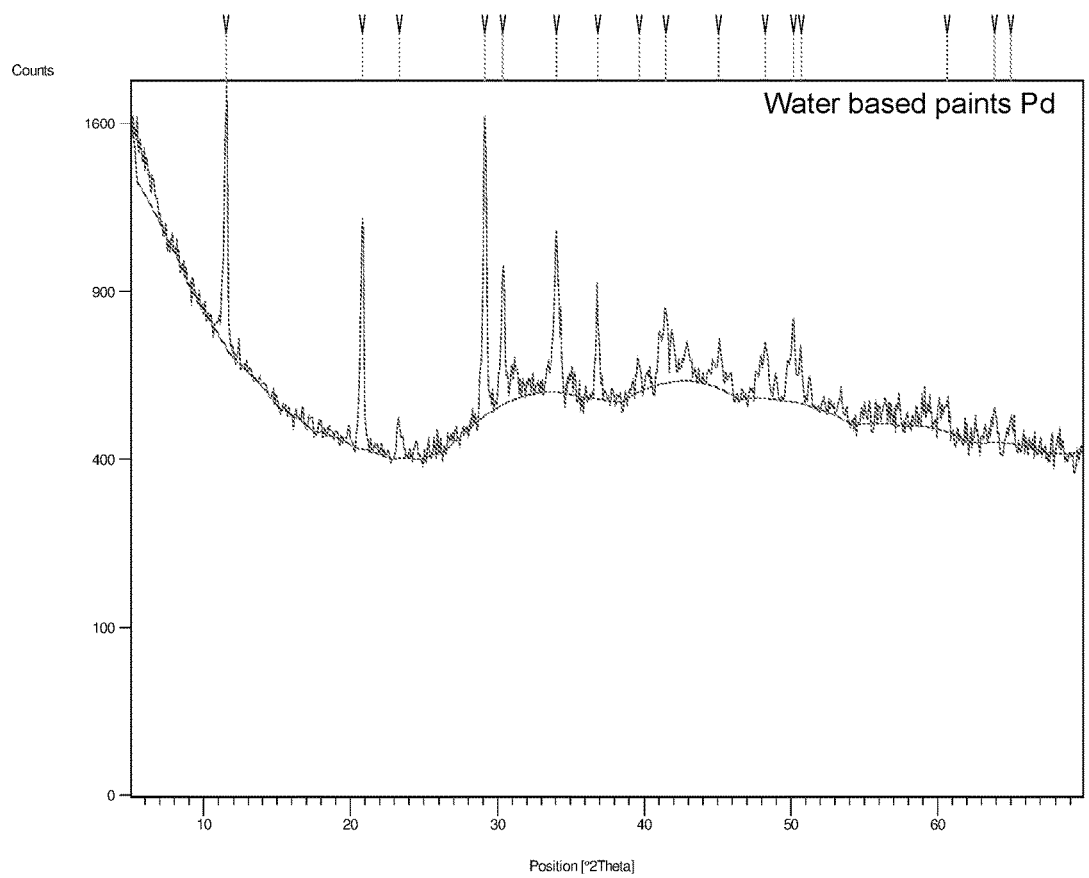
FIG. 9 shows the diffractogram of the precipitate obtained after the treatment of the example 3.

The solution resulting from the above-described process is treated with sodium hydroxide to obtain calcium phosphate as illustrated in FIG. 9, which shows the diffractogram of the precipitate from the supernatant solution.

Metals can be recovered electrochemically from the treatment of the final solution, as indicated in table 7.

TABLE 7 concentration mg/l of the metal ions recoverable electrochemically.

| Metal element | Concentration mg/l |
| --- | --- |
| Magnesium | 2097.85 |
| Iron | 106.41 |
| Nickel | 9.16 |
| Manganese | 27.60 |

The invention claimed is:

1. A process for treating an asbestos-containing material, which comprises:
    subjecting a food industry waste material to mixed bacterial and fungal growth and/or fermentation to produce an acidic solution/suspension; and
    treating an asbestos-containing material with the acidic solution/suspension at a temperature of 120-170° C. and pressure of 2-10 bar in order to produce an asbestos-containing material that is at least partially inert;
    wherein said mixed bacterial and fungal growth and/or fermentation is carried out by using bacteria of the species *Acetobacter aceti* and yeast of the species *Saccharomyces cerevisiae*.

2. The process according to claim 1, wherein said mixed bacterial and fungal growth and/or fermentation is further carried out by using one or more of the following-bacterial species selected from the group consisting of *Micrococcaceae, Propionibacteria, Bifidobacteria, Pseudomonas* spp., *Aeromonas* spp., *Photobacterium* spp., *Achromobacter* spp., *Shewanella* spp., *Xanthomonas* spp., *Vibrio* spp., *Flavobacterium* spp., *Enterobacteriaceae, Bacillus* spp., *Clostridium* spp., *Brochothrix thermosphacta*, and *Micrococcus* spp.

3. The process according to claim 1, wherein said food industry waste material is selected from the group consisting of: liquid/solid waste from vinegar production, liquid/solid waste from wine production, waste from oil production, liquid/solid waste from fruit and vegetable processing and preservation, liquid/solid waste from the production of beer, beverages and fruit-based juices, liquid waste from the oil and vegetable and animal fat refining industry, liquid/solid waste from used tea leaves and from the confectionary industry, liquid/solid waste from rice processing, liquid/solid waste from tobacco manufacturing, and combinations thereof.

4. The process according to claim 1, wherein said asbestos-containing material includes asbestos in fibril form dispersed in a friable matrix or a cement matrix, or asbestos present in a compact polymer-type matrix.

5. The process according to claim 1, wherein said asbestos-containing material is asbestos cement.

6. The process according to claim 1, wherein said mixed bacterial and fungal fermentation is carried out by incubating the food industry waste material at a temperature of between 15 and 25° C., for a time varying from a few minutes to a few days.

7. The process according to claim 1, wherein, before being treated with the acidic solution/suspension said asbestos-containing material is pulverized under water misting and vacuum conditions.

8. The process according to claim 1, wherein the treatment of the asbestos-containing material with the acidic solution/suspension is carried out by homogenizing the asbestos-containing material with the acidic solution/suspension for a period of 12-24 hours.

9. The process according to claim 1, wherein said temperature of 120-170° C. is reached by applying a temperature gradient of 20° C. to 170° C.

10. The process according to claim 1, wherein said mixed bacterial and fungal growth and/or fermentation is further carried out by using one or more of the following selected from the group consisting of lactic acid bacteria, microorganisms classified as extreme acidophiles, and acidophiles present in food industry waste.

11. The process of claim 3, wherein the waste from oil production is mill wastewater.

12. The process of claim 3, wherein the liquid/solid waste from fruit and vegetable processing and preservation is water for blanching tomato skins and citrus fruit peels.

13. The process of claim 6, wherein the time period varies from a few minutes to a few hours.

14. The process of claim 7, wherein said asbestos-containing material is pulverized under water misting and vacuum conditions to avoid or reduce any emission of asbestos fibers into the air.

15. The process of claim 7, wherein the step of pulverizing the asbestos-containing material comprises multiple steps in which the asbestos-containing material is first crushed and then pulverized into dimensions of less than one millimeter.

16. The process of claim 9, wherein the temperature gradient is applied with a single treatment cycle.

* * * * *